United States Patent [19]

Rosenthal

[11] Patent Number: 5,041,650

[45] Date of Patent: Aug. 20, 1991

[54] ALLYL SELENIDE, AND METHOD FOR MAKING AND USING

[76] Inventor: Walter Rosenthal, 525 West End Ave., 5F, New York, N.Y. 10024

[21] Appl. No.: 439,328

[22] Filed: Nov. 20, 1989

[51] Int. Cl.$^5$ .................. G01J 1/42; C07C 163/00; C07C 165/00
[52] U.S. Cl. ............................. 562/899; 356/218
[58] Field of Search .......................... 562/899

[56] References Cited

U.S. PATENT DOCUMENTS

| | | | |
|---|---|---|---|
| 1,578,731 | 3/1926 | Hochwalt | 562/899 |
| 2,398,414 | 4/1946 | Denison et al. | 562/899 |
| 2,473,511 | 6/1949 | Denison et al. | 562/899 |
| 2,577,719 | 12/1951 | Stewart | 562/899 |
| 3,678,067 | 7/1972 | Grummon et al. | 562/899 |
| 3,730,889 | 5/1973 | McCord et al. | 562/899 |
| 4,613,468 | 9/1986 | Sandman et al. | 562/899 |

FOREIGN PATENT DOCUMENTS

| | | | |
|---|---|---|---|
| 285834 | 10/1988 | European Pat. Off. | 562/899 |
| 371216 | 5/1973 | U.S.S.R. | 562/899 |
| 498315 | 1/1939 | United Kingdom | 562/899 |

OTHER PUBLICATIONS

Kataev et al., J. Org. Chem., USSR 5 (1969), p. 1478.
Zefirov, Chemica Scripta (1975) 8 A, 20–22.
Paul et al., Indian J. Chem., vol. 14A, (Nov. 1976), pp. 864–865.
The Merk Index 8th ed. (1968), p. 39.

*Primary Examiner*—J. E. Evans
*Attorney, Agent, or Firm*—Schweitzer Cornman & Gross

[57] ABSTRACT

The new compound diallyl selenide, or 3.3′-bis(1-propene)selenide, having the formula $$(CH_2=CH-CH_2)_2Se.$$

1 Claim, No Drawings

ALLYL SELENIDE, AND METHOD FOR MAKING AND USING

FIELD OF THE INVENTION

The present invention relates to the new compound diallyl selenide $[CH_2=CH-CH_2]_2Se$, and methods for its preparation and use.

BACKGROUND OF THE INVENTION

A very limited variety of organic aliphatic selenium compounds, as well as methods for their preparation have been known. C. L. Jackson in Vol. 179 Ann. Chem. [1875], pp. 1-3 describes methyl-, ethyl-, and benzylselenides and their preparation. For example, in the reduction of sodium selenide with carbon, the principal product was $(C_2H_5)_2Se_2$ along with smaller amounts of $(C_2H_5)_2Se$. Ethyldiselenide was found to be somewhat similar to methylmonoselenide.

Ethylmonoselenide was produced by Rathke Vol. 152 Ann. Chem. p. 210; Pievering, Vol. 185, Ann. Chem., p. 333, by heating a concentrated solution of $P_2Se_5$ in a complex reaction. Preparation of the end product involved the removal of the foul smelling ethyldiselenide by-product.

Other than these early publications, no evidence of other investigation in the area of organic aliphatic selenides was found.

DESCRIPTION OF THE INVENTION

The present invention concerns the new compound diallyl selenide, or 3,3'-bis(1-propene)selenide, having the formula $(CH_2=CH-CH_2)_2Se$.

The diallyl selenide containing the divalent selenium, is heavier than water.

This new compound is not even homologous to the few known organoselenides. It is liquid at room temperature and is not water soluble, exhibits the semiconductive properties of selenium in a very temperature dependent manner. Therefore, it is particularly suitable for the direct electrical sensing and measuring of temperature.

The new diallyl selenide compound is prepared by reacting a monoselenide of a metal with suitably two moles of an allyl halogenide. Iodine is preferred as the halogen, because when using chlorine or bromine, the reaction has to be carried out in a closed vessel due to their lower boiling points.

For smaller, research quantities, the new diallyl selenide compound of the present invention can be conveniently made by reacting silver selenide $Ag_2Se$ with suitably two moles of allyl iodide.

The particular reaction conditions for preparation can be determined by routine experimentation.

Methyl and alkali metal selenides are well known in the art. Sodium selenide is made by a strongly exothermic reaction of sodium when heated together with selenium. Sodium selenide can also be prepared by the reaction of its ingredients under hydrogen or in liquid ammonia, since it is soluble therein. Preparation of alkali metal selenides is well known, for example, from H. Krebs, vol. 265, Z. Anorg. Allgem. Chem. [1951] pp. 156-168; M. Hansen et al.: Constitution of Binary Alloys, 2.Ed. New York, 1958, pp. 1003-1004; and H. D. Mulder et al., Vol. 73. J. Am. Chem. Soc. [1951] pp. 5575-5577.

Silver selenide can be suitably made by reducing hot aqueous silver nitrate $AgNO_3$ by selenium to form $Ag_2Se$, and also by stirring selenium powder into a hot silver salt solution.

Suitably other selenides, such as of nickel, magnesium, iron, and of other metals can also be employed.

The new compound of the present invention can be advantageously used for the direct electrical measurement of temperature, or the intensity of light impacting thereon. A body of the diallyl selenide is contacted by at least two electrodes for measuring and/or sensing electrical characteristics of the compound. Suitably, the conductivity of the path between the electrodes is measured by application of direct current. The sharp temperature gradient of the electrical properties of diallyl selenide enables the measuring or sensing of temperature-related electrical phenomena, or the photoresistivity change as the function of impacting light intensity enables the measurement of light. The advantageously low volatility of the diallyl selenide makes it particularly useful at elevated temperatures.

Other uses of the temperature and light dependent electrical properties of the compound of the present invention will be readily apparent to persons with skill in the art.

I claim:
1. 3,3'-bis(1-propene)selenide, having the formula

$(CH_2=CH-CH_2)_2Se$.

* * * * *